United States Patent [19]
Thiel et al.

[11] Patent Number: 5,696,407
[45] Date of Patent: Dec. 9, 1997

[54] PROCESS FOR THE PRODUCTION OF SPHERULITIC PARTICLES

[75] Inventors: Klaus-Dieter Thiel, Karlsruhe; Herbert Heinisch, Ettlingen, both of Germany

[73] Assignee: Fraunhofer-Gesellschaft zur Forderung der angewandten Forschung e.V., Munich, Germany

[21] Appl. No.: 731,174

[22] Filed: Oct. 7, 1996

Related U.S. Application Data

[63] Continuation of Ser. No. 326,839, Oct. 21, 1994, abandoned.

[30] Foreign Application Priority Data

Oct. 22, 1993 [DE] Germany .................. 43 36 049.1

[51] Int. Cl.$^6$ ............................................. C06B 21/00
[52] U.S. Cl. ............... 264/3.4; 264/3.6; 149/105; 149/111; 564/262
[58] Field of Search ............. 264/3.4, 3.6; 149/105, 149/111; 564/262

[56] References Cited

U.S. PATENT DOCUMENTS

| | | | |
|---|---|---|---|
| 2,691,800 | 10/1954 | Seavey | 18/47.2 |
| 2,740,704 | 4/1956 | O'Neill, Jr. et al. | 52/20 |
| 2,850,533 | 9/1958 | O'Neall | 260/564 |
| 2,949,484 | 8/1960 | Mackay | 260/564 |
| 3,236,702 | 2/1966 | Sapiego | 149/2 |
| 3,917,767 | 11/1975 | Eich et al. | 264/3 C |
| 3,928,514 | 12/1975 | Brachert et al. | 264/3 B |
| 4,544,769 | 10/1985 | Engel et al. | 564/242 |
| 4,967,000 | 10/1990 | Sanchez et al. | 564/242 |
| 5,389,263 | 2/1995 | Gallagher et al. | 210/729 |

*Primary Examiner*—Peter A. Nelson
*Attorney, Agent, or Firm*—Antonelli, Terry, Stout & Kraus, LLP.

[57] ABSTRACT

In the production of spherulitic nitroguanidine having a high bulk and tap density nitroguanidine is dissolved in dipolar, aprotic solvents, e.g. DMF, DMSO, NMP, etc., by heating to above the saturation temperature $t_s$ and the supersaturated solution is cooled with a controlled temperature gradient (°C./min), crystallization being assisted by the addition of particulate, spherulitic material. In order to obtain spherical nitroguanidine with high yield in a continuous process and with mother liquor reuse, during the heating to above the saturation temperature $t_s$, spherical control particles with a diameter of 5 to 500 μm are regularly added to the solution in a quantity of 0.05 to 5.00 mass %. The particle size is chosen in such a way that, as a function of the solution behaviour of the nitroguanidine used and its concentration, on dropping below the saturation temperature spherical control particles are still present in the indicated quantity in the supersaturated solution.

10 Claims, 3 Drawing Sheets

FIG. 3A
FIG. 3B
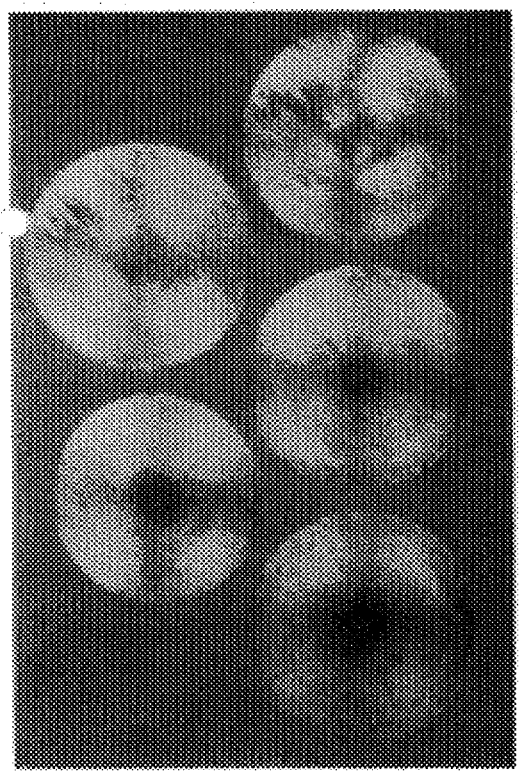
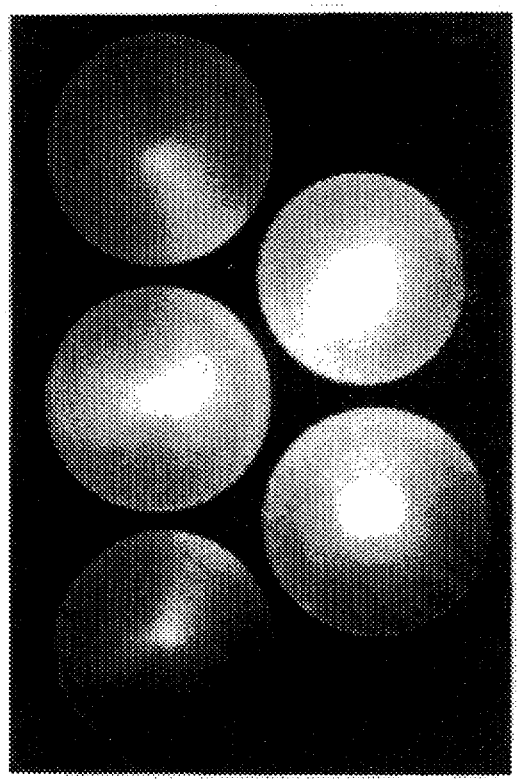

PROCESS FOR THE PRODUCTION OF SPHERULITIC PARTICLES

This application is a Continuation of application Ser. No. 08/326,839, filed Oct. 21, 1994, and now abandoned.

BACKGROUND OF THE INVENTION

The invention relates to a process for the production of spherulitic nitroguanidine having a high bulk and tap density, in that nitroguanidine is dissolved in dipolar aprotic solvents, e.g. DMF, DMSO, NMP, etc., by heating to above the saturation temperature $t_s$ and the supersaturated solution is cooled with a controlled temperature gradient (°C./min), crystallization being assisted by the addition of particulate, spherulitic material.

Nitroguanidine is used as a propellant and explosive, whose detonation velocity is higher than that of TNT and which, due to its insusceptibility to shock and higher energy density, offers certain advantages compared with conventional explosive materials. However, nitroguanidine suffers from the disadvantage that during production it is in the form of long, thin needles, which leads to numerous problems, inter alia a very low bulk density. Thus, known processes are directed at obtaining a compact crystal shape.

Thus, it is known (EP 2 740), to dissolve nitroguanidine in aliphatic alcohols, their monoalkyl or dialkyl ethers, dimethyl formamide (DMF) or dimethyl sulphoxide (DMSO) by heating to saturation temperature and, accompanied by stirring, to cool the solution at a temperature gradient of more than 3 K/min., crystallization starting at temperatures below 50° C. In addition, a recrystallization process is described, in which the hot nitroguanidine solution is poured into a second, cold solvent, in which nitroguanidine is not or is only soluble with difficulty. Although this process leads to more compact nitroguanidine crystals, the yield of ideal spherical nitroguanidine is small.

In the first-mentioned process (DE 3,527,200), the starting product is once again a hot, saturated solution, which is circulated with a clearly defined stirring efficiency and in which during the cooling phase and prior to the start of self-nucleation, intrinsic seed particles with a diameter of >50 µm are added. However, also in this process the ideal spherical nitroguanidine yield is low.

Both the aforementioned processes can only be carried out on a technical scale in batch operation and exclusively with fresh batches, which are therefore prepared from fresh nitroguanidine and solvents. However, it is not possible to reuse the mother liquor and the latter must be disposed of after each crystallization process. This leads to a high raw material use, with low economics and environmental incompatibility.

SUMMARY OF THE INVENTION

The problem of the invention is to so further develop the first-mentioned process that nitroguanidine is obtained as a spherical crystallizate with a high yield and in particular in which the mother liquor can be returned to the crystallization process.

According to the invention this problem is solved in that, during heating to above the saturation temperature $t_s$, regularly spherical control particles with a diameter of 5 to 500 µm are added to the solution in a quantity of 0.05 to 5.00 mass %, said particle size being chosen in such a way that, as a function of the solution behaviour of the nitroguanidine used and its concentration, on dropping below the saturation temperature spherical control particles are still present in the supersaturated solution in the indicated quantity.

BRIEF DESCRIPTION OF THE DRAWINGS

FIG. 3 shows macrophotographs of a crystallizate obtained by the method according to the invention.

DETAILED DESCRIPTION OF THE PREFERRED EMBODIMENTS

Figure 1:
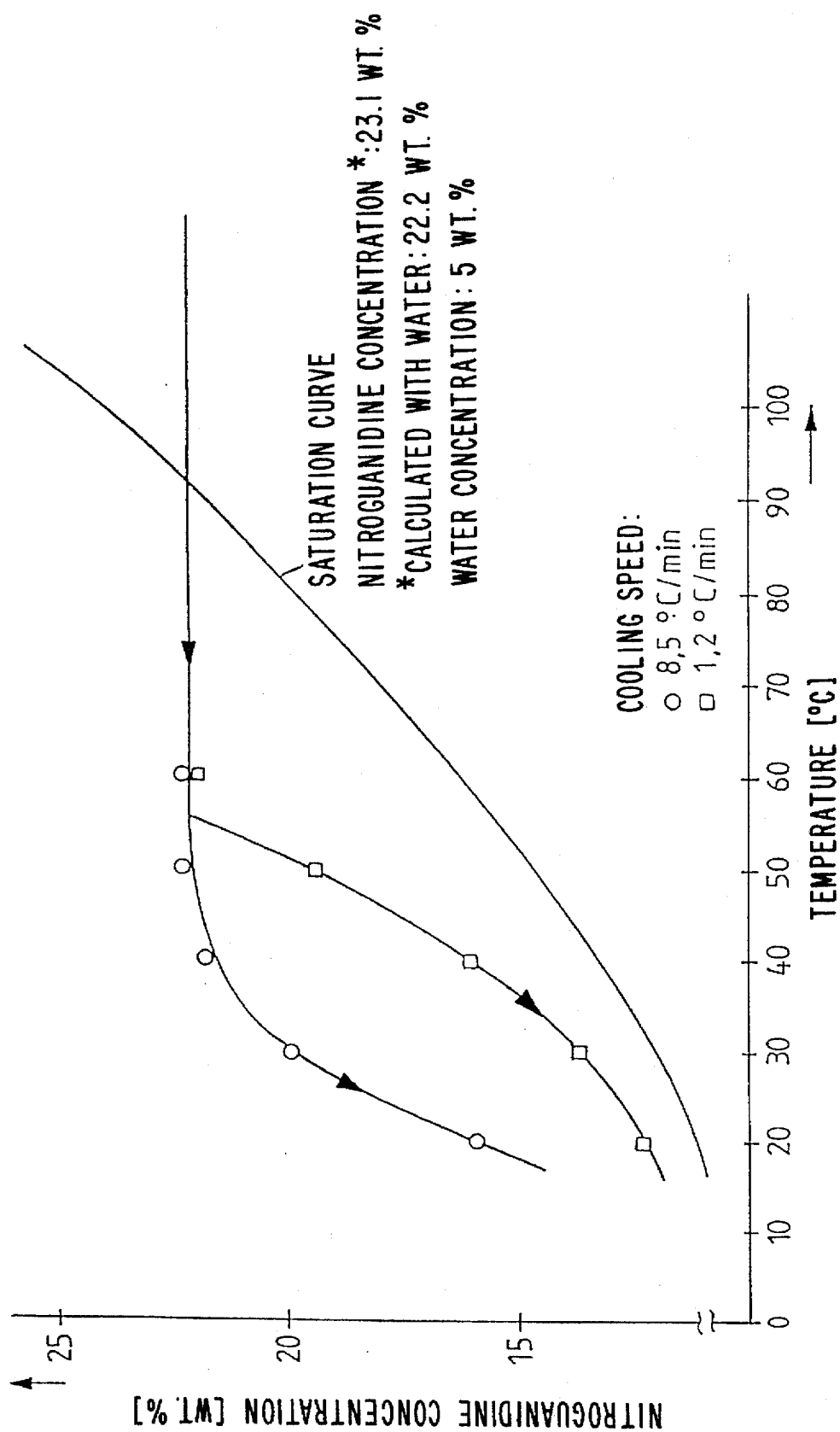
FIG. 1 shows in a diagrammatical view the concentration course of Nitroguanidine during cooling with two different cooling rates.

Seeding with in particular intrinsic seed particles known in crystallization technology is the intentional introduction of nuclei into the supersaturated or supercooled mother phase. This seeding always takes place during the cooling process in solution-cooling-crystallization, including in the first-mentioned process (DE 3,527,200). Unlike in the case of conventional seeding, in the process according to the invention regularly spherical control particles are added to the warming phase or to the start of the cooling phase and prior to reaching the saturation temperature.

These particles control and check during the cooling the states in the mother liquor after exceeding the saturation limit and eliminate disturbing influences, e.g. as a result of existing or forming unfavourable structures in the mother liquor or through impurities. The control action of the particles is ended as soon as the formation of new and clearly defined, regular nuclei initiated by conditioning starts and they then spontaneously continue to grow. It is also possible to avoid the formation of so-called nuclear clouds occurring at low temperature, i.e. a very large number of nuclei, which very rapidly lead to agglomerates. The control particles leads to a kinetically defined crystallization, so that supersaturation is controlled in a defined manner. However, with a kinetically undefined crystallization the quality of the crystallizate is subject to the random kinetic interactions. The defined addition of control particles under defined conditions to the hot, unsaturated solution is referred to as the conditioning of the residual solution.

The prerequisite for this function of the control particles is its regular spherical shape and its size limited to a diameter of 5 to 500 µm, as well as its quantity of 0.05 to 5.00 mass %. If the control particles are added during the warming phase, then the particle size will tend to be larger, so as to take account of the dissolving process acting on the control particles and so as to have in the cooling phase control particles with an adequately large size. However, if the control particles are added at above the saturation temperature during the commencing cooling phase, generally smaller particles will be chosen, so that the control particles are not significantly dissolved. For the initial dissolving of the control particles and therefore for the choice of the particle size vital attention is not only paid to the residence time until dropping below the saturation temperature, but also the solution behaviour of the nitroguanidine used and its concentration. The influence of these parameters on the choice of the particle size can easily be determined by testing.

Preferably the control particles are added in a temperature range between $t_s$ and $t_s+50$ K, i.e. towards the end of the warming phase or the start of the cooling phase.

In such a procedure it has proved advantageous to add control particles with a diameter of 60 to 90 μm and in a quantity of 0.4 mass %. The precipitating crystallizate is absolutely spherical and has a dense structure, so that high bulk density and tap density nitroguanidine is obtained.

It is also advantageous to use as the control particles spherical nitroguanidine, so as to avoid different types of chemical or mechanical influences on the crystallizate.

It has also proved advantageous to cool the supersaturated solution with a temperature gradient of >0.5 K/min., the concentration drop below the saturation temperature at low cooling rates approximately following the saturation curve, whereas a greater supersaturation can be set for high cooling speeds.

The process according to the invention offers the possibility of concentrating with nitroguanidine the mother liquor left behind after the crystallization process and, accompanied by further addition of control particles, to again heat it to above the saturation temperature and subject it to a further crystallization process. Practical tests have revealed that the mother liquor can be recirculated up to 10 times without the crystallizate quality suffering or the yield being reduced. Through the addition of fresh solution and mixing of recycled mother liquor, the number of crystallization cycles can be increased.

To facilitate understanding, FIG. 1 shows the nitroguanidine concentration course during cooling for two different cooling speeds. The concentration curve passes horizontally through the saturation curve. With a small cooling speed of 1.2° C./min., the concentration drops very rapidly in a medium temperature range. Nucleation starts spontaneously. The concentration drop is decisively influenced by the course of the saturation curve. For higher cooling speeds of 8.5° C./min., there is a much greater supersaturation in the solution and nucleation starts later.

A number of tests are reproduced below.

Production of the Control Particles

TABLE 1

| Material system | |
|---|---|
| * Nitroguanidine/NMP (N-methyl-pyrrolidone) | |
| Nitroguanidine concentration | ξNigu: 25.9 mass % |
| Water concentration (addition) | ξw : 4.5 mass % |
| Cooling speed | ζ': 3.8 °C./min |
| Crystal-nucleation temperature | ζK,B: 50° C. |
| Crystallization final temperature | ζK,E: 20° C. |
| Residence time at final temperature | ζK,E: 10 min |
| Particle shape | : spherical, smooth surface |

Production of Spherical Nitroguanidine

TABLE 2

| Material system | |
|---|---|
| * Nitroguanidine/DMF (dimethyl formamide) Fresh batch | |
| Concentration nitroguanidine | ξNigu: 24.5 mass % |
| Cooling rate | ζ': 4.6° C./min |
| Crystal-nucleation temperature | ζK,B: 49° C. |

TABLE 2-continued

| | |
|---|---|
| Crystallization final temperature | ζK,E: 20° C. |
| Nitroguanidine concentration at | ζK,E: 16.1 mass % |
| Supersaturation at | ζK,E: 1.32 |
| Tap density σK | : 0.95 g/cm³ |
| Yield φ | : 42.9% |
| Particle shape Φ | : spherical, smooth surface |

| Batches with mother liquor reuse (without conditioning) | | |
|---|---|---|
| Nitroguanidine concentration | ξNigu: | 23.1 mass % |
| Cooling rate | ζ': | 4.6° C./min |
| Crystal-nucleation temperature | ζK,B: | 49° C. |
| Crystallization final temperature | ζK,E: | 20° C. |
| Nitroguanidine concentration at | ζK,E: | 14.2 mass % |
| Supersaturation at | ζK,E: | 1.13 |
| Particle shape Φ | : | irregular |
| Tap density σK | : | not determined due to poor particle shape |
| Yield | : | |

TABLE 3

| Material system | |
|---|---|
| * Nitroguanidine/DMF Fresh batch | |
| Nitroguanidine concentration | ξNigu: 24.5 mass % |
| Cooling speed | ζ': 4.6° C./min |
| Crystal-nucleation temperature | ζK,B: 49° C. |
| Crystallization final temperature | ζK,E: 20° C. |
| Nitroguanidine concentration at | ζK,E: 16.1 mass % |
| Supersaturation at | ζK,E: 1.32 |
| Particle shape Φ | : spherical, smooth surface |
| Tap density σK | : 0.95 g/cm³ |
| Yield φ | : 42.5% |

| Batches with mother liquor reuse (with conditioning). | |
|---|---|
| Nitroguanidine concentration | ξNigu: 23.1 mass % |
| Cooling speed | ζ': 4.6° C./min |
| Addition of control particles: | |
| Nitroguanidine, recrystallized, concentration of control particles χS,K (related to the dissolved material quantity) | : 0.4 mass % |
| Particle size for control particles χS,K | : (63–90) μm |
| Particle shape Φ at temperature ζS,K | : spherical, smooth : 95° C. |
| Crystal-nucleation temperature (turbidity point) ζK,B | : 67° C. |
| Crystallization final temperature | ζK,E: 20 ° C. |
| Nitroguanidine concentration at | ζK,E: 15 mass % |
| Supersaturation at ζK,E | : 1.19 |
| Particle shape Φ | : spherical, smooth surface |
| Tap density σK | : 0.94 g/cm³ |
| Yield φ | : 40.5% |
| * Temperature at saturation concentration $t_s$ | : 93° C. |

TABLE 4

Material system

* Nitroguanidine/NMP
Fresh batch

| | |
|---|---|
| Nitroguanidine concentration | ξNigu: 29.8 mass % |
| Cooling speed | ζ': 3.7° C./min |
| Crystal-nucleation temperature | ζK,B: 54° C. |
| Crystallization final temperature | ζK,E: 20° C. |
| Nitroguanidine concentration at ζK,E | 25.3 mass % |
| Supersaturation at ζK,E | 1.45 |
| Residence time at ζK,E | : 30 min |
| Particle shape σ | : spherical, smooth surface |
| Tap density ΦK | : 1.10 g/cm³ |
| Yield φ | : 10.5% |

Batches with Mother Liquor Reuse (With Conditioning)

| | |
|---|---|
| Nitroguanidine concentration | ξNigu: 25.9 mass % |
| Cooling speed | ζ': 3.4° C./min |
| Addition of control particles: | |
| Nitroguanidine, recrystallized, concentration ξS,K (based on dissolved material quantity) | : 0.4 mass % |
| Particle size χS,K | : (63–90) μm |
| Particle shape σ | : spherical, smooth surface |
| at temperature ζS,K | : 97° C. |
| Crystal-nucleation temperature (turbidity point) ζK,B | : 75° C. |
| Crystallization final temperature ζK,E | : 20° C. |
| Nitroguanidine concentration at ζK,E | : 21.8 mass % |
| Supersaturation at ζK,E | : 1.25 |
| Particle shape Φ | : spherical, smooth |
| Tap density σK | : 0.99 g/cm³ |
| Yield φ | : 23.7% |
| * Temperature at saturation concentration $t_s$ | : 95° C. |

Table 1 summarizes the essential data for producing the control particles, which are characterized by a spherical shape and a smooth surface.

The test according to Table 2 shows in the upper part for the nitroguanidine/DMF system and with a fresh batch a good spherulitic particle shape, as well as a good tap density and yield. The lower part gives the test data and results for batches concomitantly using the mother liquor from the test in the upper part of the Table. This gives a very irregular particle shape, so that the tap density and yield were not determined.

In upper part of Table 3 are given the test data and results for a fresh batch of the nitroguanidine/DMF system. Once again with a fresh batch there is a high quality particle shape, as well as a satisfactory tap density and yield. The lower part of the Table gives the results when reusing the mother liquor and adding control particles. The Table shows that, despite the reuse of the mother liquor, neither the particle shape, nor the tap density and yield suffered. For the same cooling speed there is a lower supersaturation than with the fresh batch. The statistical evaluation of the test series has generally shown that the less low the supersaturation the closer the spherical particle shape comes to the ideal shape, or conversely the lower the supersaturation the worse the particle shape and therefore the tap density.

Table 4 gives the same test data and results for the nitroguanidine/NMP system. Here again the conditioning with the control particles shows that, despite the reuse of the mother liquor, the crystallizate particle shape is not negatively influenced and an only insignificantly lower tap density is made good by a much higher yield.

Figure 2A:
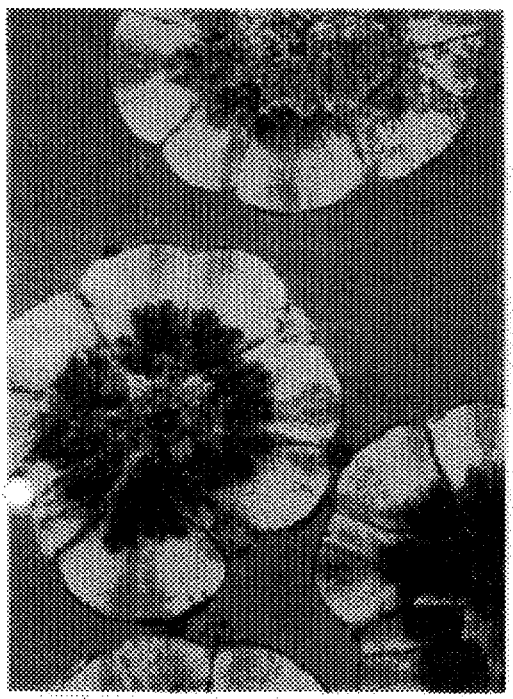
FIGS. 2A and 2B are shows macrophotographs of a crystallizate produced according to the art.
Figure 2B:

FIGS. 2A and 2B are shows macrophotographs of a crystallizate obtained from a solution batch accompanied by the concomitant use of mother liquor, but without adding control particles (e.g. Table 2, lower part), whereas FIGS. 3A and 3B are shows a crystallizate obtained in accordance with the invention, i.e. with conditioning by spherical control particles.

We claim:

1. A process for the production of spherulitic nitroguanidine having a high bulk and tap density, comprising:

forming a solution by dissolving nitroguanidine in a dipolar aprotic solvent by heating to above the saturation temperature;

adding regularly spherical control particles to the solution; and cooling the solution having the regularly spherical control particles therein to below the saturation temperature at a controlled temperature gradient;

wherein the regularly spherical control particles are added in an amount and with a particle diameter such that, on dropping below the saturation temperature during the cooling, the regularly spherical control particles have a diameter of 5 to 500 μm and are present in an amount of 0.05 to 5.00 mass %, wherein crystallization of the nitroguanidine is assisted by the regularly spherical control particles to yield a crystallizate of nitroguanidine having a spherical shape and high bulk and tap density.

2. Process according to claim 1, characterized in that the regularly spherical control particles are added in a temperature range between the saturation temperature and the saturation temperature +50 K.

3. Process according to claim 1, characterized in that the regularly spherical control particles are added with a diameter of 60 to 90 μm.

4. Process according to claim 3, characterized in that the regularly spherical control particles are added in a quantity of 0.4 mass %.

5. Process according to claim 1, characterized in that spherical nitroguanidine is used as the regularly spherical control particles.

6. Process according to claim 1, characterized in that the supersaturated solution is cooled with a temperature gradient >0.5° C./min.

7. Process according to claim 1, for the continuous production of spherulitic nitroguanidine, characterized in that the mother liquor left following the crystallization process is concentrated with nitroguanidine and heated to above the saturation temperature again, accompanied by the addition of regularly spherical control particles.

8. Process according to claim 1, wherein said dipolar aprotic solvent is selected from the group consisting of DMF, DMSO and NMP.

9. Process according to claim 1, wherein the regularly spherical particles are added during the cooling prior to reaching the saturation temperature.

10. Process according to claim 1, wherein the regularly spherical particles are added during the heating to above the saturation temperature.

* * * * *